United States Patent [19]
Shen

[11] Patent Number: 5,320,949
[45] Date of Patent: Jun. 14, 1994

[54] PROCESS FOR PRODUCING AGLUCONE ISOFLAVONE ENRICHED VEGETABLE PROTEIN FIBER

[75] Inventor: Jerome L. Shen, St. Louis, Mo.

[73] Assignee: Protein Technologies International, Inc., St. Louis, Mo.

[21] Appl. No.: 135,193

[22] Filed: Oct. 12, 1993

[51] Int. Cl.⁵ .................... C12P 21/00; C12P 21/06
[52] U.S. Cl. .................... 435/68.1; 252/404; 252/407; 426/546; 435/76; 435/125; 435/200; 435/272; 514/2; 514/455; 530/378; 536/8; 549/402; 549/403
[58] Field of Search ............ 435/68.1, 200, 123, 435/125, 76, 272; 536/8; 530/378; 514/2, 455; 549/402, 403; 426/546; 252/398, 404, 407

[56] References Cited

U.S. PATENT DOCUMENTS

| | | | |
|---|---|---|---|
| 3,949,085 | 4/1976 | Feuer et al. | 424/283 |
| 4,157,984 | 6/1979 | Zilliken | 252/407 |
| 4,163,746 | 8/1979 | Feuer et al. | 260/345.2 |
| 4,218,489 | 8/1980 | Zilliken | 426/545 |
| 4,232,122 | 11/1980 | Zilliken | 435/52 |
| 4,264,509 | 4/1981 | Zilliken | 260/345.2 |
| 4,366,082 | 12/1982 | Zilliken | 252/404 |
| 4,366,248 | 12/1982 | Zilliken | 435/125 |
| 4,390,559 | 6/1983 | Zilliken | 426/545 |
| 4,399,224 | 8/1983 | Flider et al. | 435/271 |
| 4,428,876 | 1/1984 | Iwamura | 260/123.5 |
| 4,841,077 | 6/1989 | Ito et al. | 549/402 |
| 4,960,908 | 10/1990 | Ito et al. | 549/403 |

OTHER PUBLICATIONS

Aps Abstract Japan Patent JP04-266898 (Feb. 3, 1993 Abs. Pub Date) "Soybean Isoflavone Glucoside."
Proceedings Of The American Association For Cancer Research, vol. 34, Mar. 1993, Abstracts 999 and 3310.
"Genistein and Biochanin A Inhibit the Growth of Human Prostate Cancer Cells But Not The Epidermal Growth Factor Receptor Tyrosin Autophosphorylation" by Peterson and Barnes; The Prostate, 22:335-345 (1993).
"Soybean Inhibit Mammary Tumors In Models Of Breast Cancer" by Barnes et al; Mutagens and Carcinogens in the Diet, pp. 239-253 (1990).
"Genistein Inhibition Of The Growth Of Human Breast Cancer Cells: Independence From Estrogen Receptors and the Multi-Drug Resistance Gene" by Peterson and Barnes: Biochemical and Biophysical Research Communications, vol. 179, pp. 661-667.
"Genistein, a Specific Inhibitor of Tyrosine Specific Protein Kinases" by Akiyama et al; The Journal of Biological Chemistry, vol. 262, 12, pp. 5592-5595; 1987.
"Mechanisms of Action In NIH-3T3 Cells Of Genistein, An Inhibitor Of EGF Receptor Tyrosin Kinase Activity" by Linassier et al; Biochemical Pharmacology, vol. 39, No. 1, pp. 187-193 (1990).
"The Role of Soy Products in Reducing Risk of Cancer" by Messina and Barnes; Journal of the National Cancer Institute, vol. 83, No. 8, pp. 541-545 (1991).
"Effect of Genistein on Topoisomerase Activity And On The Growth Of [VAL 12]" Ha-ras Transformed NIH 3T3 Cells by Okura, et al.; Biochemical and Biophysical Research Communications, vol. 157, No. 1, pp. 183-189 (1988).
"Induction of Mammalian Topoisomerase II Dependent DNA Cleavage By Nonintercalative Flavonoids", Genistein and Orobol by Yamashita, et al; Biochemical Pharmacology, Vo. 39, No. 4, pp. 737-744 (1990).
Soybean Utilization (1987) pp. 64-66.
Soybeans: Chemistry and Technology (1978) pp. 187-188.

Primary Examiner—Herbert J. Lilling
Attorney, Agent, or Firm—Virgil B. Hill

[57] ABSTRACT

The present invention relates to an aglucone isoflavone enriched vegetable protein fiber wherein a vegetable protein material is extracted to form a slurry of protein, fiber and glucone isoflavones. The pH of the slurry is adjusted to about 6 to 8 and the slurry reacted with a beta glucosidase to convert the glucone isoflavones in said slurry to aglucone isoflavones. The fiber fraction is then recovered from the slurry by centrifugation or similar means to provide an aglucone enriched fiber.

6 Claims, No Drawings

PROCESS FOR PRODUCING AGLUCONE ISOFLAVONE ENRICHED VEGETABLE PROTEIN FIBER

BACKGROUND OF THE INVENTION

The present invention relates to an aglucone isoflavone enriched vegetable protein fiber and process for producing the same.

Isoflavones occur in a variety of leguminous plants, including vegetable protein materials such as soybeans. These compounds include diadzin, 6O AC daidzin, daidzein, genistin, 6OAC genistin, genistein, glycitin, biochanin A, formonoetin, and coumestrol. Typically these compounds are associated with the inherent, bitter flavor of soybeans, and in the production of commercial products, such as isolates and concentrates, the focus has been to remove these materials. For example, in a conventional process for the production of a soy protein isolate, in which soy flakes are extracted with an aqueous alkaline medium, much of the isoflavones are solubilized in the extract, and remains solubilized in the whey, which is usually discarded following acid precipitation of the protein, to form an isolate. Residual isoflavones left in the acid precipitated protein isolate are usually removed by exhaustive washing of the isolate.

It has been recently recognized that the isoflavones contained in vegetable proteins such as soybeans may inhibit the growth of human cancer cells, such as breast cancer cells and prostrate cancer cells as described in the following articles: "Genistein Inhibition of the Growth of Human Breast Cancer Cells; "Independence from Estrogen Receptors and the Multi-Drug Resistance Gene" by Peterson and Barnes *Biochemical and Biophysical Research, Communications*; Vol. 179, No. 1, pp. 661–667, August 30, 1992; "Genistein and Biochanin A Inhibit the Growth of Human Prostate Cancer Cells but not Epidermal Growth Factor Receptor Tyrosine Auto-phosphorylation" by Peterson and Barnes: The Prostate 22: pp. 335–345 (1993) and "Soybeans Inhibit Mammary Tumors in Models of Breast Cancer" by Barnes, et al. Mutagens and Carcinogens in the Diet; p. 239-253 (1990).

Of the above isoflavones, several exist as glucosides, or as glucones, with a glucose molecule attached. Several of the glucones such as the 6OAC genistin, contain an acetate group attached to the six position of the glucose molecule itself. While all of the isoflavones, including the glucosides are of interest in medical evaluation, the specific isoflavones of most interest are the aglucones, wherein the glucose molecule is not attached. These isoflavones are not as water soluble as the glucones or isoflavone glucosides. Specific isoflavones in this category are daidzein, genistein, and glycitein. These aglucones have the following general formula,

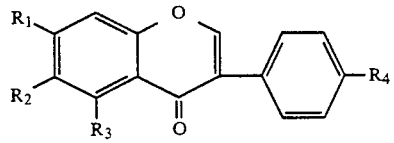

wherein, $R_1$, $R_2$, $R_3$ and $R_4$ may be selected from the group consisting of H, OH and $OCH_3$. It is therefore to the aglucones and enrichment of a vegetable protein fiber such as the spent flake residue from a soy isolate process with these materials to which the present invention is directed.

It is therefore an object of the present invention to provide an aglucone isoflavone enriched protein fiber, and a process for producing the same. This, and other objects, are specifically achieved in the detailed description of the present invention set forth below.

SUMMARY OF THE INVENTION

The present invention relates to a process for producing an aglucone isoflavone enriched fiber from a vegetable protein material. A aqueous slurry is formed of the vegetable protein material, wherein the pH is maintained above about the isoelectric point of the protein, preferably about 6.0–10.0. Protein, soluble carbohydrates, and isoflavones are solubilized, with the fibrous material remaining as an insoluble residue. The pH of the slurry is then adjusted to pH of about 6 to 8 and reacted with a beta-glucosidase for a time and temperature sufficient to convert substantially all of the glucone isoflavones to aglucone isoflavones, which are less soluble at the noted pH range therefore are retained with the fibrous residue after recovery thereof to provide an aglucone enriched fiber product. The aglucone enriched fiber product can be dewatered to form a dried, aglucone enriched fiber product.

DESCRIPTION OF THE PREFERRED EMBODIMENTS

Although the present invention will be described with respect to soybean products, and the process is particularly suited for the production of aglucone isoflavone enriched fiber products from soybean materials, nevertheless the process is generally applicable to the production of fibres from a variety of vegetable protein sources which contain isoflavones.

The starting material for the instant invention is soybean flour, from which the oil has been removed by solvent extraction. The flakes are slurried with an aqueous extractant having a pH above about he isoelectric point of the protein material, preferably a pH of about 6.0–10.0 and a most preferred pH of about 6.7 to 9.7. Typical alkaline reagents, may be employed, if desired to elevate the pH of the aqueous extractant including sodium hydroxide, potassium hydroxide, and calcium hydroxide. The desired isoflavone compounds are typically solubilized in the aqueous extractant. It is desirable, also, in order to maximize recovery of these compounds in the aqueous extract that the weight ratio of soybean flakes to extract is controlled to specific levels in order to solubilize as much of the inherent isoflavones in the protein material as possible.

Extraction of the isoflavones can be carried out in a variety of ways including countercurrent extraction of the flakes at a weight ratio of flakes to aqueous extract of about 8:1 to 16:1, in which the initial extract is used to reextract the flakes and provide an aqueous extract of protein and isoflavones. Alternatively, a two step extraction process can be used in which the weight ratio of flakes to extractant in the initial step comprises about 10:1 and then a second extraction of the flakes with fresh extractant takes place at a weight ratio of flakes to extractant of about 6:1, so that the combined weight ratio of flakes to extractant is both steps does not exceed a total weight ratio of flakes to extractant of about 16.1. The pH of the aqueous slurry is then adjusted to about 6 to 8.

The resulting aqueous slurry with solubilized isoflavones is then reacted with a beta-glucosidase in order to convert substantially all of the isoflavones in glucone form, with a glucose molecule attached, to an aglucone isoflavone. The optimum pH range for the beta-glucosidase will vary depending on the specific beta-glucosidase used, but typically will be within the range described above. The pH is typically adjusted by the addition of an edible acid, such as acetic, sulfuric, phosphoric, hydrochloric, or any other suitable reagent.

The pH adjusted slurry with solubilized isoflavones is reacted with a beta-glucosidase for a time and temperature sufficient to convert substantially all of the glucone isoflavones contained in the slurry to the aglucone form. The beta-glucosidase is preferably "Lactozym" available from NOVO Industries, Enzyme Division, NOVO Alle, DK-2880 Bagsvaerd, Denmark, which has an optimum pH range of about 7, and is added in an amount sufficient to convert substantially all of the glucone isoflavones to aglucones. Preferably the amount of enzyme added is about 0.5 to 5% by weight of the protein material on a dry basis. Typical, non-limiting times and temperatures for reaction is about 40° to 60° C. for about 2 to 34 hours.

Following conversion to the aglucone, which is a much less soluble form of isoflavone at the noted pH range, the fibrous residue is recovered from the soluble material to provide a soybean fiber product, which has been enriched with aglucone isoflavones. The soybean fiber product which is the residual product from the production of soy protein isolate is typically referred to as the spent flake residue and it is composed of cellulosic and hemicellulosic materials. This material has a relatively high insoluble dietary fiber content and a relatively low soluble dietary fiber content. This soybean fiber product has a protein content on a dry basis of about 19%, an ash content on a dry basis of about 4% by weight, and a density of about 15 lb/cu.ft. after drying.

The enriched fiber product containing aglucones can be readily recovered by conventional means including centrifugation, or filtration. The recovered product may also be dewatered to provide a dried product, by conventional drying techniques. The present invention provides an aglucone enriched fiber product having a genistein content of about 1.0 and 2.0 mg/g and a daidzein content of about 0.7 to 1.7 mg/g.

The following Examples describe specific but non-limiting embodiments of the present invention.

EXAMPLE 1

100 g of defatted soy flour was slurried with 1,000 g of water, which has been adjusted to a pH of 9.5 by the additional of sodium hydroxide for 15 minutes at a temperature of 38° C.

The pH of the slurry was then lowered to 6.5 by the addition of hydrochloric acid. Two percent by weight of the soy flour of "Lactozyme" was added. "Lactozyme" is an enzyme having beta-glucosidase activity available from NOVO Industries, Enzyme Division, NOVO Alle, DK2880 Bagswood, DENMARK. The slurry was allowed to react for 20 hours at 38° C. The slurry was centrifuged to remove the spent flour. The spent flour residue was resuspended in 6 parts of water at pH 8.0 and 38° C. for 10 minutes. The slurry is again centrifuged to recover the spent flour. The first and second extracts are combined and the pH adjusted to 4.5 by the addition of hydrochloric acid to precipitate the problems. The protein curd is separated from the whey by centrifugation.

Analysis of curd, whey, spent flakes and starting material was completed for the aglucone isoflavones genistein and daidzein, as well as their glucoside or glucone forms genistin and daidzin. Analysis of these aglucone isoflavones was accomplished by the procedure described below.

ANALYSIS PROCEDURE

1. Standard solutions were prepared by dissolving 0.500 mg of genistein, and daidzein into a 100 ml volumetric flask with 80 parts methyl alcohol, and 20 parts water. This provides a concentration of each individual isoflavone in the standard solution of 5 micrograms/ml.

2. 0.25 gm of soy product is weighed out, and extracted with 100 ml of 80 parts methyl alcohol and 20 parts water by stirring for 10 minutes.

3. The slurry is sonicated on high power (400 watts) for 5 minutes, then on low power (100 watts) for 15 minutes, and finally on high power for 5 minutes.

4. The solution is filtered through a Whatman #4 filter and rinsed to a total volume of 100 ml.

5. 6.25 ml of the filtrate is transferred to a heat tube, and 3.75 ml of millipone water added. 0.2 ml of acetic acid is added, the solution is mixed.

6. The sample solution is injected onto a high pressure liquid chromatography column, and measured by comparison to the standard solution by UV absorption.

Analysis of the curd, soy whey, spent flakes, and starting material for the above isoflavone set forth in Table 1. The results are also shown as a percentage recovery of the noted isoflavones from the level contained in the starting material.

TABLE 1

| | Level (mg/g Dry Basis) | | | | % Recovery | |
|---|---|---|---|---|---|---|
| Material | Genistein | Genistin$^a$ | Daidzein | Daidzin$^b$ | Genistein$^c$ | Daidzein$^d$ |
| Curd | 1.03 | N.A. | 0.80 | N.A. | 22% | 19% |
| Whey | 0.53 | N.A. | 0.89 | N.A. | 16% | 30% |
| Fiber Spent Flour | 1.46 | N.A. | 1.07 | N.A. | 62% | 51% |
| Starting Material | 0.02 | 1.70 | 0.02 | 1.55 | | |

$^a$Genistin plus 60AC Genistin
$^b$Daidzin plus 60AC Daidzin
$^c$Total of Genistin, 60AC Genistin, and Genistein
$^d$Total of Daidzin, 60AC Daidzin, and Daidzein
N.A. - Not analyzed It is apparent that conversion of substantially all of the glucone to the aglucone form has been carried out together with a concentration of the aglucones in the spent flour to provide a fiber material enriched with aglucone isoflavones.

Numerous variations and equivalents to the present invention will be readily apparent to one skilled in the art.

What is claimed is:

1. A process of producing an aglucone isoflavone enriched fiber from a vegetable protein material comprising:
   a. forming an aqueous slurry of a vegetable protein material containing fiber and glucone isoflavones at pH above about the isoelectric point of the material;
   b. adjusting the pH of said slurry to about 6 to 8;
   c. reacting said slurry with a sufficient amount of beta-glucosidase for a time and temperature sufficient to convert substantially all of the glucone isoflavone material in said slurry to an aglucone isoflavone; and d. recovering an aglucone enriched fiber from said slurry.

2. The process of claim 1 wherein the pH of said extractant is about 6–10.0.

3. The process of claim 2 wherein extraction is carried out at a pH of about 6.7 to 9.7.

4. The process of claim 1 wherein the vegetable protein material is soybeans.

5. The process of claim 1 wherein the pH is adjusted to about 6 to 8.

6. The process of claim 1 wherein recovery of said fiber is carried out by centrifugation of said slurry.

* * * * *